(12) United States Patent
Maruyama et al.

(10) Patent No.: US 9,874,523 B2
(45) Date of Patent: *Jan. 23, 2018

(54) SURFACE-ENHANCED RAMAN SCATTERING ELEMENT INCLUDING A CONDUCTOR LAYER HAVING A BASE PART AND A PLURALITY OF PROTUSIONS

(71) Applicant: HAMAMATSU PHOTONICS K.K., Hamamatsu-shi, Shizuoka (JP)

(72) Inventors: Yoshihiro Maruyama, Hamamatsu (JP); Katsumi Shibayama, Hamamatsu (JP); Masashi Ito, Hamamatsu (JP); Toru Hirohata, Hamamatsu (JP); Hiroki Kamei, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/420,422

(22) PCT Filed: Aug. 9, 2013

(86) PCT No.: PCT/JP2013/071698
§ 371 (c)(1),
(2) Date: Feb. 9, 2015

(87) PCT Pub. No.: WO2014/025029
PCT Pub. Date: Feb. 13, 2014

(65) Prior Publication Data
US 2015/0212000 A1 Jul. 30, 2015

(30) Foreign Application Priority Data
Aug. 10, 2012 (JP) .................................. 2012-178765

(51) Int. Cl.
G01N 21/65 (2006.01)
G01N 21/03 (2006.01)
B82Y 40/00 (2011.01)

(52) U.S. Cl.
CPC ............ G01N 21/658 (2013.01); G01N 21/03 (2013.01); B82Y 40/00 (2013.01); G01N 2201/068 (2013.01)

(58) Field of Classification Search
CPC ...... G01N 21/65; G01N 21/658; B82Y 15/00; B82Y 40/00
See application file for complete search history.

(56) References Cited

U.S. PATENT DOCUMENTS 9,127,984 B2 * 9/2015 Tseng .................. G01N 21/658
2004/0023046 A1 2/2004 Schlottig et al.
(Continued)

FOREIGN PATENT DOCUMENTS

| CN | 101281133 | 10/2008 |
|----|-----------|---------|
| CN | 101319994 | 12/2008 |

(Continued)

OTHER PUBLICATIONS

"Q-SERS™ G1 Substrate," Opto Science, Inc. (retrieved on-line on Jul. 5, 2013).
(Continued)

Primary Examiner — Michael A Lyons
Assistant Examiner — Violeta A Prieto
(74) Attorney, Agent, or Firm — Drinker Biddle & Reath LLP

(57) ABSTRACT

A SERS element comprises a substrate; a fine structure part formed on a front face of the substrate and having a plurality of pillars; and a conductor layer formed on the fine structure part and constituting an optical function part for generating surface-enhanced Raman scattering. The conductor layer
(Continued)

has a base part formed along the front face of the substrate and a plurality of protrusions protruding from the base part at respective positions corresponding to the pillars. The base part and the protrusions form a plurality of gaps in the conductor layer, each of the gaps having an interstice gradually decreasing in a direction perpendicular to the projecting direction of the pillar.

9 Claims, 18 Drawing Sheets

(56) References Cited

U.S. PATENT DOCUMENTS

| | | | |
|---|---|---|---|
| 2006/0146323 | A1 | 7/2006 | Bratkovski et al. |
| 2008/0094621 | A1 | 4/2008 | Li et al. |
| 2008/0218761 | A1 | 9/2008 | Nishikawa et al. |
| 2010/0019355 | A1 | 1/2010 | Kamins et al. |
| 2011/0027901 | A1 | 2/2011 | Gaster et al. |
| 2011/0116089 | A1 | 5/2011 | Schmidt et al. |
| 2011/0166045 | A1 | 7/2011 | Dhawan et al. |
| 2011/0267607 | A1 | 11/2011 | Hu et al. |
| 2012/0081703 | A1 | 4/2012 | Moskovits et al. |
| 2014/0043605 | A1* | 2/2014 | Tseng .......... G01J 3/44 356/301 |
| 2014/0045209 | A1 | 2/2014 | Chou et al. |
| 2014/0154668 | A1* | 6/2014 | Chou .......... B82Y 15/00 435/5 |
| 2015/0211999 | A1* | 7/2015 | Maruyama ...... G01N 21/658 356/301 |
| 2015/0212002 | A1* | 7/2015 | Ito .......... G01N 21/658 359/241 |
| 2015/0212003 | A1* | 7/2015 | Shibayama ...... G01N 21/658 356/244 |
| 2015/0219562 | A1* | 8/2015 | Shibayama ...... G01N 21/658 356/244 |
| 2015/0233832 | A1* | 8/2015 | Maruyama ...... G01N 21/658 356/244 |
| 2015/0233833 | A1* | 8/2015 | Shibayama ...... G01N 21/658 356/244 |
| 2015/0338346 | A1* | 11/2015 | Chou .......... B82Y 15/00 435/287.2 |

FOREIGN PATENT DOCUMENTS

| | | |
|---|---|---|
| CN | 101529229 | 9/2009 |
| CN | 102282094 | 12/2011 |
| CN | 102348066 | 2/2012 |
| CN | 102483354 | 5/2012 |
| JP | H05-044867 U | 6/1993 |
| JP | H07-260646 A | 10/1995 |
| JP | 2003-026232 A | 1/2003 |
| JP | 2005-337771 A | 12/2005 |
| JP | 2007-530925 A | 11/2007 |
| JP | 2007-538264 A | 12/2007 |
| JP | 2008-519254 A | 6/2008 |
| JP | 2008-196992 A | 8/2008 |
| JP | 2008-268059 A | 11/2008 |
| JP | 2009-025316 A | 2/2009 |
| JP | 2009-047623 A | 3/2009 |
| JP | 2009-103643 A | 5/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141265 A | 7/2011 |
| JP | 2011-215021 A | 10/2011 |
| JP | 2012-233707 A | 11/2012 |
| TW | 201410591 | 3/2014 |
| WO | WO-2007/149120 A2 | 12/2007 |
| WO | WO-2010/050203 A1 | 5/2010 |
| WO | WO-2010/090111 A1 | 8/2010 |
| WO | WO-2011/021085 A2 | 2/2011 |
| WO | WO-2011/040504 A1 | 4/2011 |
| WO | WO-2012/024006 A2 | 2/2012 |
| WO | WO 2013/015810 | 1/2013 |
| WO | WO-2014/025033 A1 | 2/2014 |
| WO | WO-2014/025034 A1 | 2/2014 |

OTHER PUBLICATIONS

Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.
International Search Report dated Nov. 12, 2013, issued in International Application No. PCT/JP2013/071695.
International Search Report dated Nov. 5, 2013, issued in International Application No. PCT/JP2013/071696.
International Search Report dated Nov. 5, 2013, issued in International Application No. PCT/JP2013/071698.
International Search Report dated Nov. 5, 2013, issued in International Application No. PCT/JP2013/071700.
International Search Report dated Nov. 19, 2013, issued in International Application No. PCT/JP2013/071702.
International Search Report dated Nov. 12, 2013, issued in International Application No. PCT/JP2013/071703.
International Search Report dated Nov. 5, 2013, issued in International Application No. PCT/JP2013/071709.
International Search Report dated Nov. 5, 2013, issued in International Application No. PCT/JP2013/071710.
International Search Report dated Apr. 28, 2014, issued in International Application No. PCT/JP2014/052926.
International Search Report dated May 13, 2014, issued in International Application No. PCT/JP2014/052928.
W. Zhang et al., "Giant and uniform fluorescence enhancement over large areas using piamonic nanodots in 3D resonant cavity nanoantenna by nanoimprinting". Nanotechnolgy, vol. 23, No. 22, May 10, 2012, p. 225301, XP020224099.
S. M. Wells et al., "Efficient disc on pillar substrates for surface enhanced Raman spectroscopy", Chemical Communications—Chemcom, vol. 47, No. 13, Jan. 1, 2011, p. 3814-3816, XP055289549.
U.S. Office Action dated Oct. 14, 2016 that issued in U.S. Appl. No. 14/420,510 including Double Patenting Rejections on pp. 2-14.
K. Nakamoto et al., "Arrays of Metallic Nanopillars in Holes for Plasmonic Devices", Retrieved from the Internet: URL: http://www.rse.org/images/LOC/2011/PDFs/Papers/596_0021.pdf, Oct. 6, 2011, XP055289892.
M. Tomohiko et al., "New localized surface plasmon resonance sensor utilizing nanoimprinting technology", NSTI Nanotechnology Conference and Trade Show-NSTI Nanotech, vol. 1, May 11, 2006, p. 58-61, XP009098538.
W. D. Li et al "Three-dimensional cavity nanoantenna coupled plasmonic nanodots for ultrahigh and uniform surface-enhanced Raman scattering over large area", Optics Express, vol, 19, No. 5, Feb. 14, 2011, p. 3925-3916. XP002751299.
U.S. Office Action dated Dec. 10, 2015 that issued in U.S. Appl. No. 14/420,404 including Double Patenting Rejections on pp. 12-15.

* cited by examiner

Fig.6
(a)
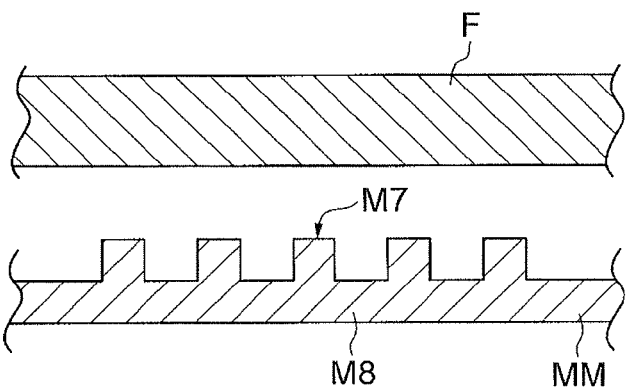
(b)
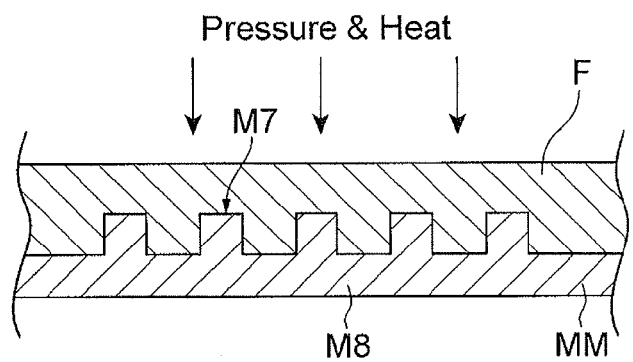
(c)
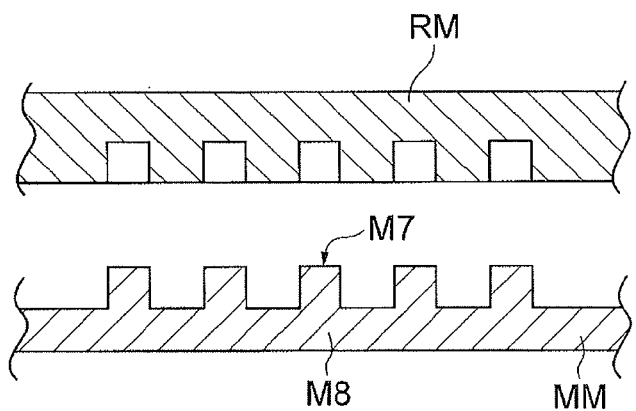

*Fig.7*
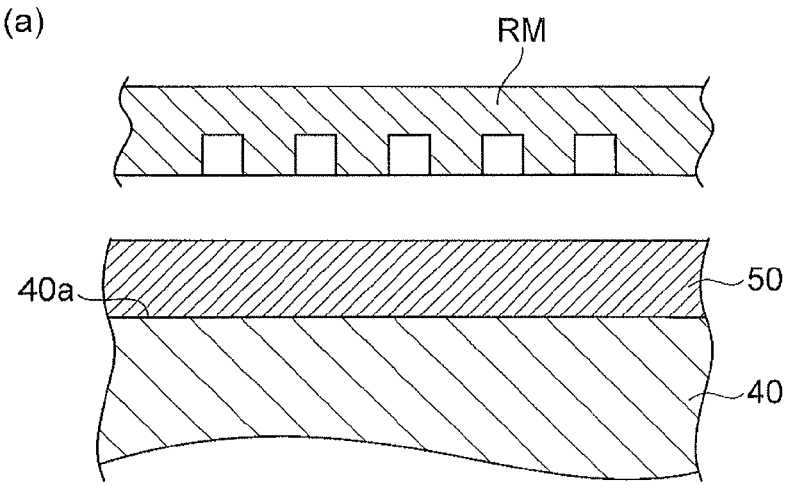
(a)
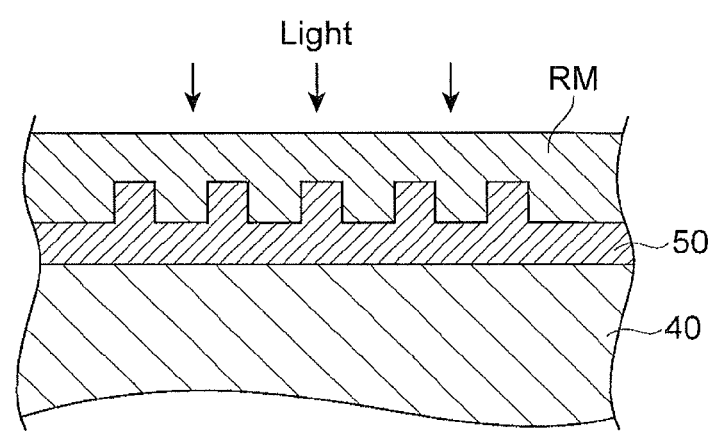
(b)
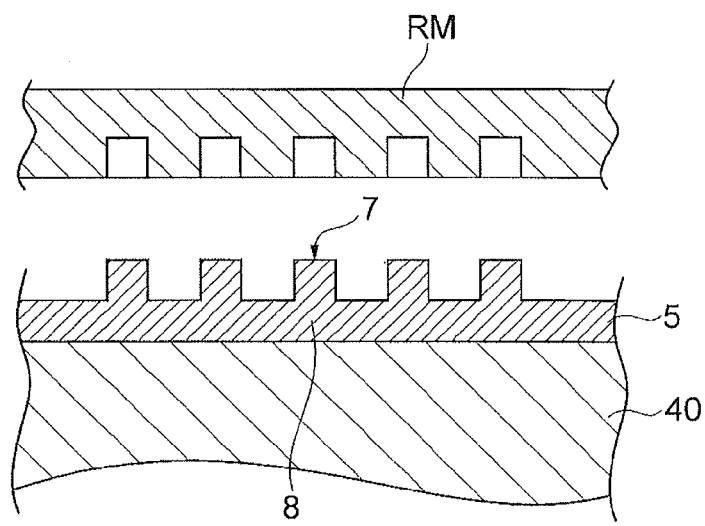
(c)

50nm

50nm

Fig. 14
(a)
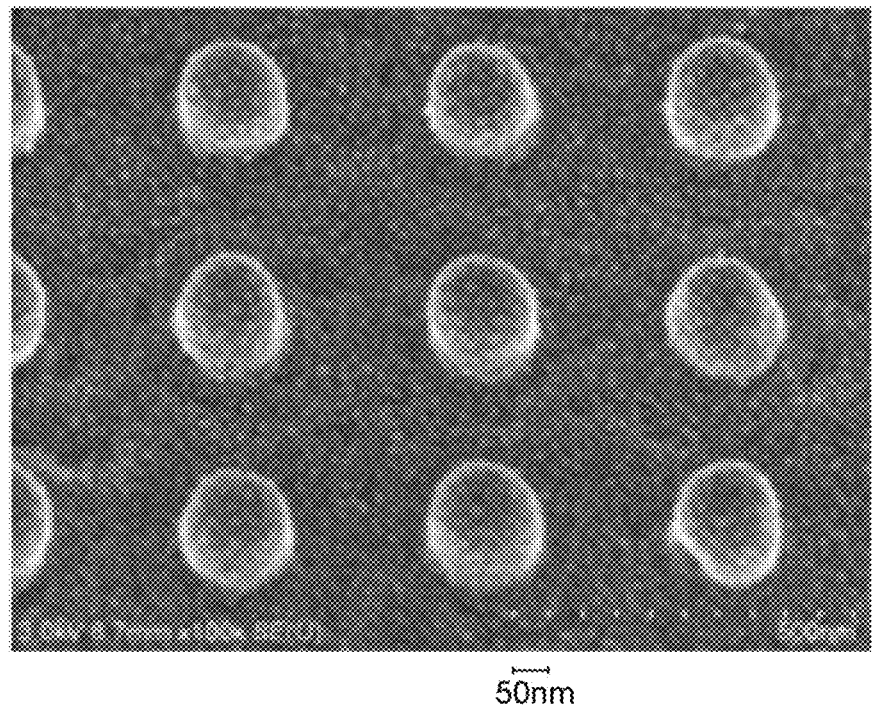
50nm
(b)
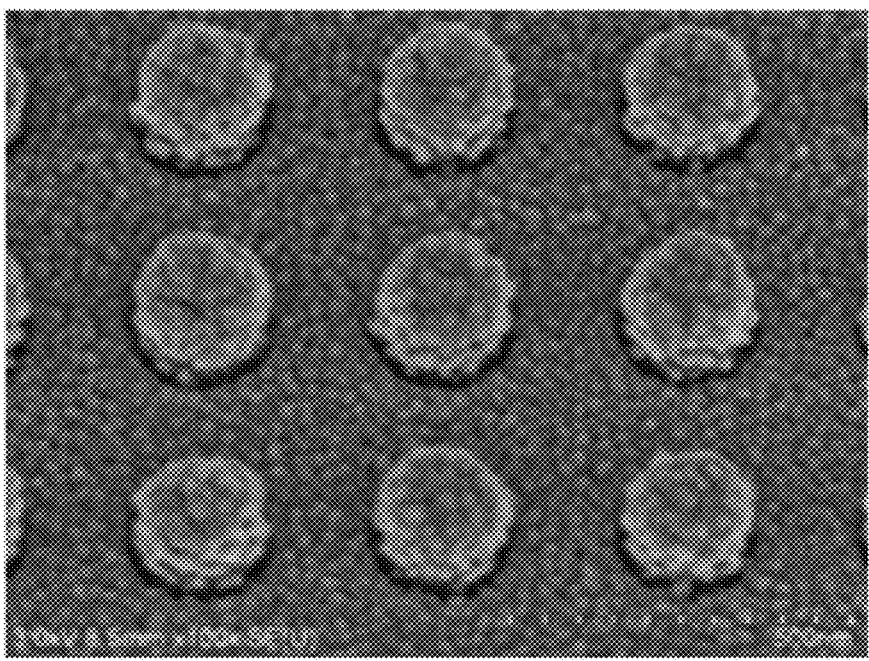
50nm

Fig.17
(a)
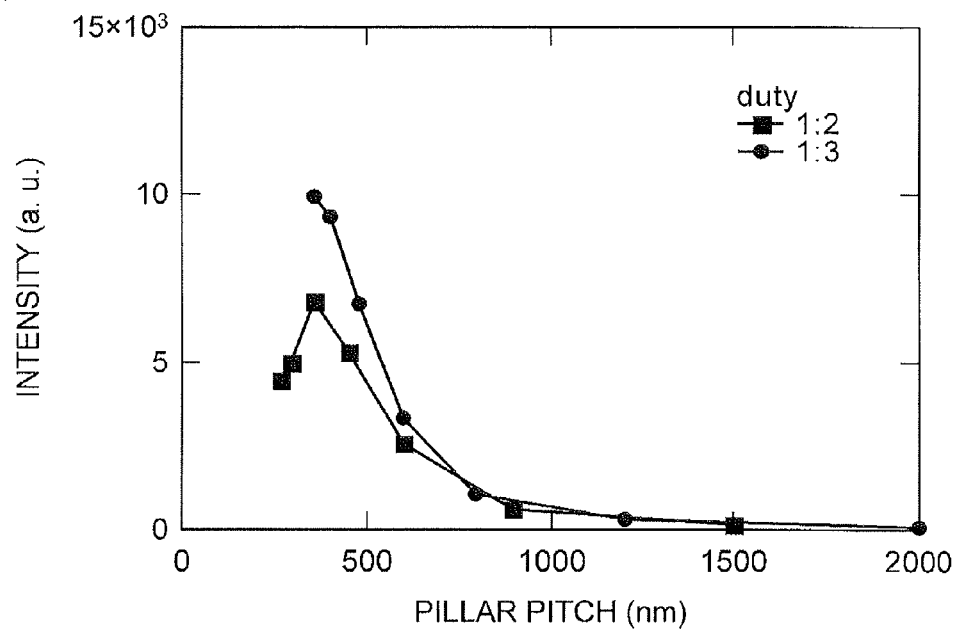
(b)
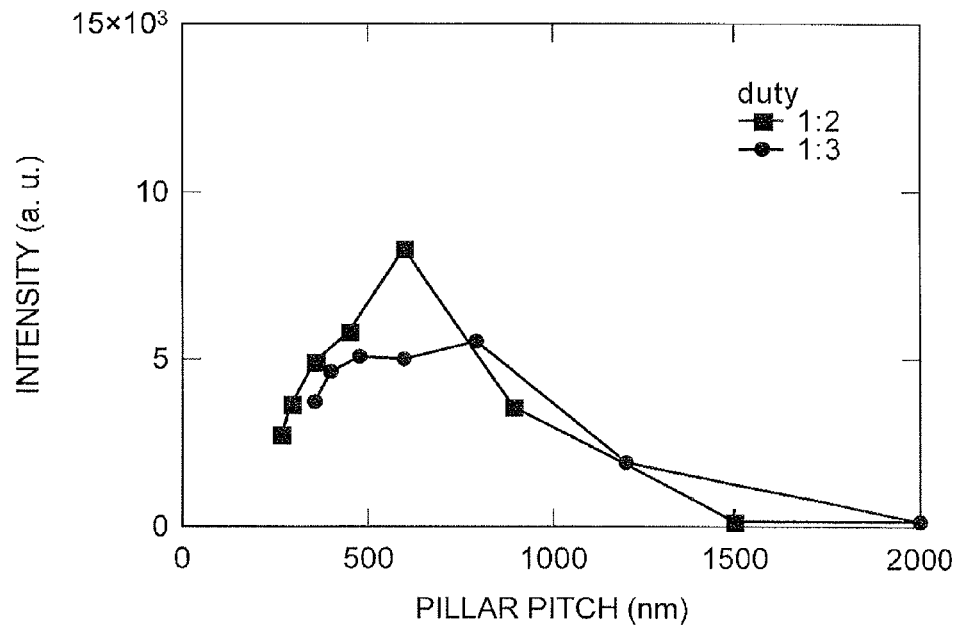

SURFACE-ENHANCED RAMAN SCATTERING ELEMENT INCLUDING A CONDUCTOR LAYER HAVING A BASE PART AND A PLURALITY OF PROTUSIONS

TECHNICAL FIELD

The present invention relates to a surface-enhanced Raman scattering element.

BACKGROUND ART

As a conventional surface-enhanced Raman scattering element, one equipped with a minute metal structure configured to generate surface-enhanced Raman scattering (SERS) has been known (see, for example, Patent Literature 1 and Non Patent Literature 1). In such a surface-enhanced Raman scattering element, when a sample to be subjected to Raman spectroscopic analysis is brought into contact with the minute metal structure and is irradiated with excitation light in this state, surface-enhanced Raman scattering occurs, whereby Raman scattering light enhanced by about $10^8$ times, for example, is released.

Meanwhile, for example, Patent Literature 2 discloses a minute metal structure in which metal layers are formed on one surface of a substrate and upper faces of a plurality of minute projections formed on the one surface of the substrate (or bottom faces of a plurality of fine holes formed on the one surface of the substrate) so as to be out of contact with each other (such that the shortest distance therebetween is on the order of 5 nm to 10 μm).

CITATION LIST

Patent Literature

Patent Literature 1: Japanese Patent Application Laid-Open No. 2011-33518
Patent Literature 2: Japanese Patent Application Laid-Open No. 2009-222507

Non Patent Literature

Non Patent Literature 1: "Q-SERS™ G1 Substrate", [online], Opto Science, Inc., [retrieved on 2012 Jul. 19]. Retrieved from the Internet: <URL: http://www.optoscience.com/maker/nanova/pdf/Q-SERS_G1.pdf>.

SUMMARY OF INVENTION

Technical Problem

When a minute metal structure is formed with a so-called nanogap as mentioned above, electric fields are locally enhanced upon irradiation with excitation light, whereby the intensity of surface-enhanced Raman scattering increases.

It is therefore an object of the present invention to provide a surface-enhanced Raman scattering element which can increase the intensity of surface-enhanced Raman scattering by a favorable nanogap.

Solution to Problem

The surface-enhanced Raman scattering element in accordance with one aspect of the present invention comprises a substrate having a principal surface; a fine structure part formed on the principal surface and having a plurality of projections; and a conductor layer formed on the fine structure part and constituting an optical function part for generating surface-enhanced. Raman scattering; the conductor layer having a base part formed along the principal surface and a plurality of protrusions protruding from the base part at respective positions corresponding to the projections; the base part and protrusions forming a plurality of gaps in the conductor layer, each of the gaps having an interstice gradually decreasing in a direction perpendicular to the projecting direction of the projections.

In this surface-enhanced Raman scattering element, the base part and protruding parts form a plurality of gaps, each of the gaps having an interstice gradually decreasing in a direction perpendicular to the projecting direction of the projections, in the conductor layer constituting the optical function part. The gaps formed in this conductor layer favorably function as nanogaps where electric fields are enhanced. Therefore, this surface-enhanced Raman scattering element can increase the intensity of surface-enhanced Raman scattering by favorable nanogaps.

In the surface-enhanced Raman scattering element in accordance with one aspect of the present invention, the projections may be arranged periodically along the principal surface. This configuration can increase the intensity of surface-enhanced Raman scattering.

In the surface-enhanced Raman scattering element in accordance with one aspect of the present invention, the gaps may be formed so as to surround the respective projections when seen in the projecting direction of the projections and each of the gaps may have the interstice gradually decreasing at an end part on the substrate side. This configuration can increase the gaps favorably functioning as nanogaps.

In the surface-enhanced Raman scattering element in accordance with one aspect of the present invention, the interstice of the gap may gradually decrease continuously. This configuration enables the gaps formed by the base part and protrusions to function securely as nanogaps.

In the surface-enhanced Raman scattering element in accordance with one aspect of the present invention, the protrusion may have a form constricted at an end part on the substrate side. This configuration can easily and securely yield the gap gradually decreasing the interstice in a direction perpendicular to the projecting direction of the projections.

In the surface-enhanced Raman scattering element in accordance with one aspect of the present invention, the base part may have a thickness either smaller or greater than a height of the projections. Either configuration can increase the intensity of surface-enhanced Raman scattering by favorable nanogaps.

In the surface-enhanced Raman scattering element in accordance with one aspect of the present invention, the base part and protrusion may be either connected to each other or separated from each other at the deepest part of the gap. Either configuration can increase the intensity of surface-enhanced Raman scattering by favorable nanogaps.

Advantageous Effects of Invention

The present invention can provide a surface-enhanced Raman scattering element which can increase the intensity of surface-enhanced Raman scattering by a favorable nanogap.

BRIEF DESCRIPTION OF DRAWINGS

FIG. 6 is a sectional view illustrating steps of manufacturing the surface-enhanced Raman scattering element of FIG. 1;

FIG. 7 is a sectional view illustrating steps of manufacturing the surface-enhanced Raman scattering element of FIG. 1;

FIG. 14 is a SEM photograph of the optical function part in the surface-enhanced Raman scattering element of Example 5;

FIG. 17 is a graph illustrating relationships between pillar pitch and signal intensity concerning the surface-enhanced Raman scattering elements of Examples 2 and 5.

DESCRIPTION OF EMBODIMENTS

Figure 1:
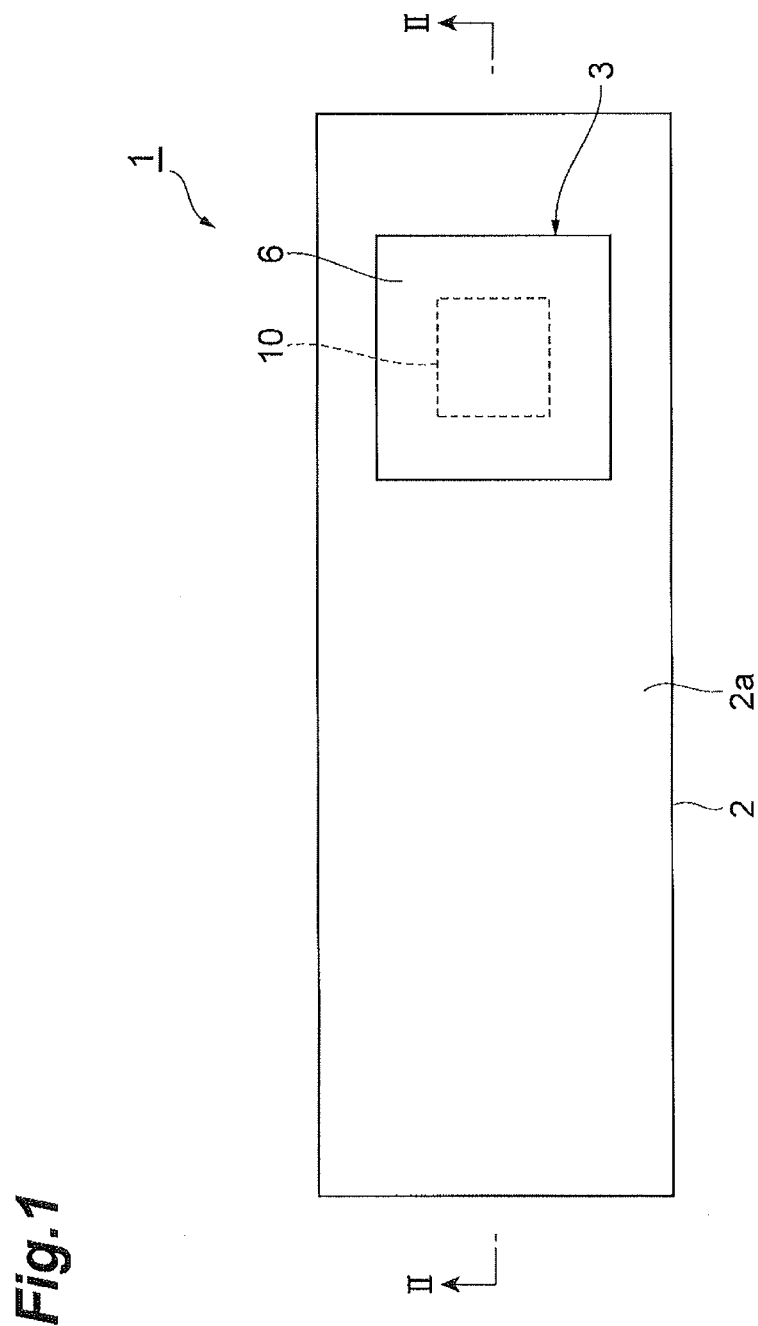
FIG. 1 is a plan view of a surface-enhanced Raman scattering unit equipped with a surface-enhanced Raman scattering element in accordance with an embodiment of the present invention.

In the following, preferred embodiments of the present invention will be explained in detail with reference to the drawings. In the drawings, the same or equivalent parts will be referred to with the same signs while omitting their overlapping descriptions.

Figure 2:
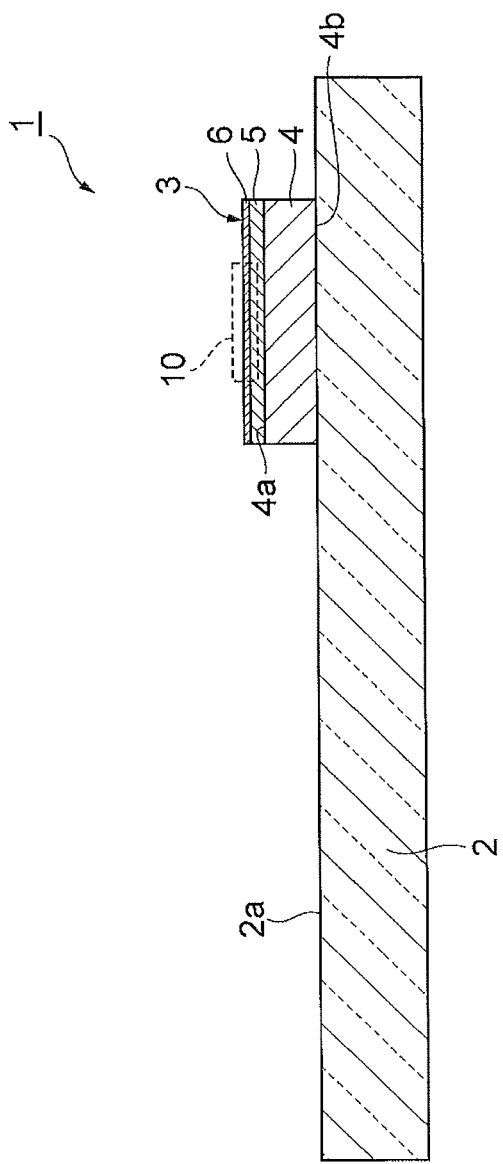
FIG. 2 is a sectional view taken along the line II-II of FIG. 1.

As illustrated in FIGS. 1 and 2, a SERS unit (surface-enhanced Raman scattering unit) 1 comprises a handling board 2 and a SERS element (surface-enhanced Raman scattering element) 3 attached onto the handling board 2.

The handling board 2 is a rectangular plate-shaped glass slide, resin board, ceramic board, or the like. The SERS element 3 is arranged on a front face 2a of the handling board 2 while being biased to one end part in the longitudinal direction of the handling board 2.

The SERS element 3 comprises a substrate 4 attached onto the handling board 2, a molded layer 5 formed on the substrate 4, and a conductor layer 6 formed on the molded layer 5. The substrate 4 is formed into a rectangular plate by silicon, glass, or the like and has an outer form on the order of several hundred μm×several hundred μm to several ten mm×several ten mm and a thickness on the order of 100 μm to 2 mm. A rear face 4b of the substrate 4 is secured to the front face 2a of the handling board 2 by direct bonding, bonding with a metal such as solder, eutectic bonding, fusion bonding by irradiation with laser light and the like, anodic bonding, or bonding with a resin.

Figure 3:
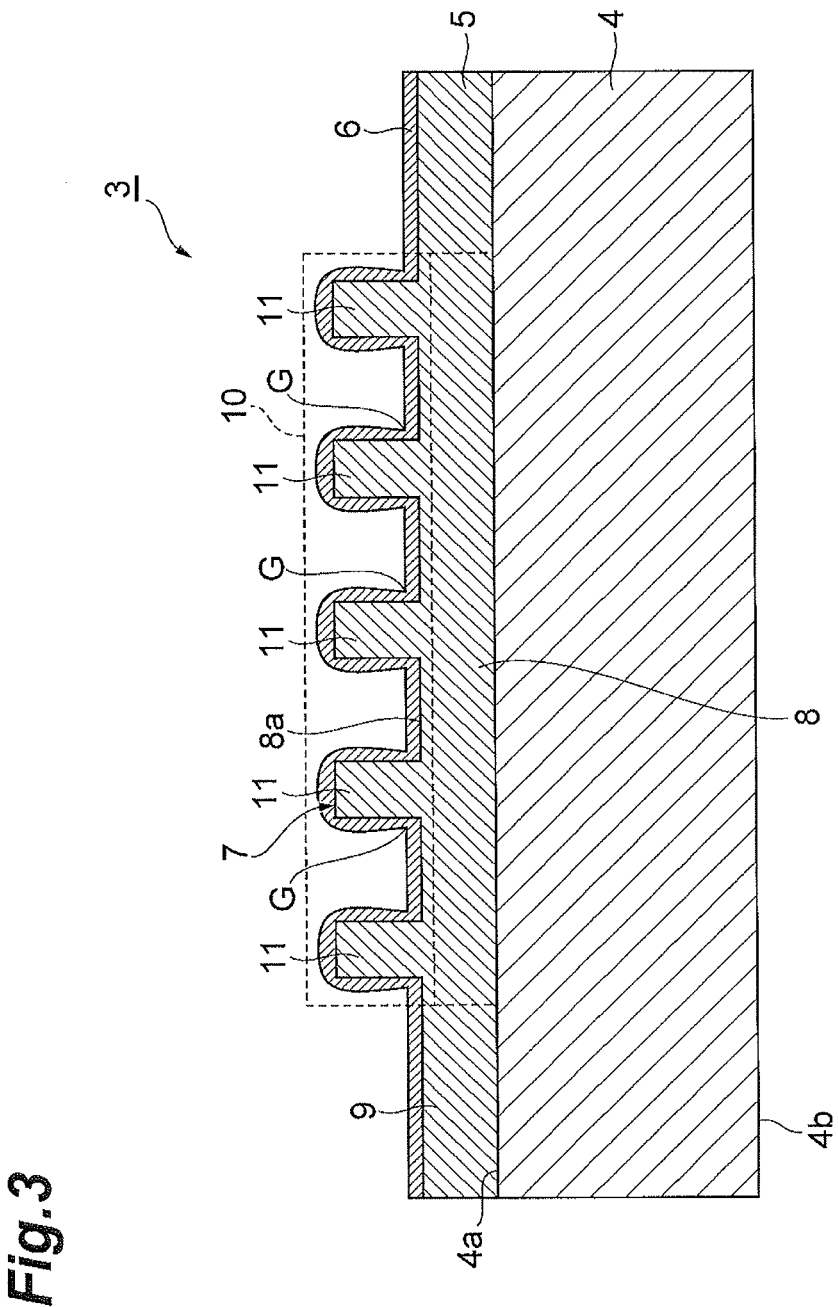
FIG. 3 is a vertical sectional view of an optical function part in the surface-enhanced Raman scattering element of FIG. 1.

As illustrated in FIG. 3, the molded layer 5 includes a fine structure part 7, a support part 8, and a frame part 9. The fine structure part 7, which is a region having a periodic pattern, is formed on a surface layer on the side opposite from the substrate 4 at a center part of the molded layer 5. In the fine structure part 7, a plurality of circular columnar pillars (projections) 11, each having a diameter and height on the order of several nm to several hundred nm, are periodically arranged at a pitch on the order of several ten nm to several hundred nm (preferably 250 nm to 800 nm) along a front face (principal surface) 4a of the substrate 4. The fine structure part 7 has a rectangular outer form on the order of several mm×several mm when seen in the thickness direction of the substrate 4. The support part 8, which is a rectangular region supporting the fine structure part 7, is formed on the front face 4a of the substrate 4. The frame part 9, which is a rectangular ring-shaped region surrounding the support part 8, is formed on the front face 4a of the substrate 4. The support part 8 and frame part 9 have a thickness on the order of several ten nm to several ten μm. The molded layer 5 like this is integrally formed by molding a resin (examples of which include resins based on acrylics, fluorine, epoxy, silicone, and urethane, PET, polycarbonate, and inorganic/organic hybrid materials) or low-melting glass arranged on the substrate 4 by nanoimprinting, for example.

The conductor layer 6 is formed over the fine structure part 7 and frame part 9. In the fine structure part 7, the conductor layer 6 reaches a surface 8a of the support part 8 which is exposed to the side opposite from the substrate 4. The conductor layer 6 has a thickness on the order of several nm to several μm. The conductor layer 6 like this is formed by vapor-depositing a conductor such as a metal (Au, Ag, Al, Cu, Pt, or the like) on the molded layer 5 molded by nanoimprinting, for example. In the SERS element 3, the conductor layer 6 formed on the fine structure part 7 and the surface 8a of the support part 8 constructs an optical function part 10 which generates surface-enhanced Raman scattering.

Figure 4:
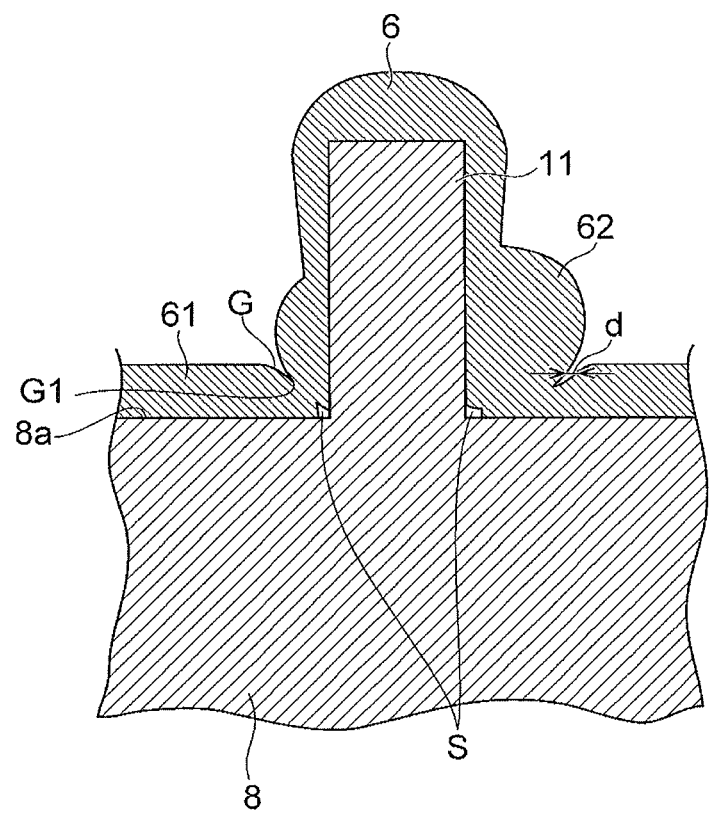
FIG. 4 is a vertical sectional view of a pillar and a conductor layer in the optical function part of FIG. 3.

As illustrated in FIG. 4, the conductor layer 6 has a base part 61 formed along the front face 4a of the substrate 4 and a plurality of protrusions 62 protruding from the base part 61 at respective positions corresponding to the pillars 11. The base part 61 is formed like a layer on the surface 8a of the support part 8. The base part 61 has a thickness on the order of several nm to several hundred nm, which is smaller than the height of the pillars 11. Each protrusion 62 is formed so as to cover its corresponding pillar 11 and has a form constricted at least at an end part on the substrate 4 side. The end part on the substrate 4 side of the protrusion 62 is located closer to the substrate than is the upper face of the base part 61.

In the conductor layer 6, the base part 61 and protrusions 62 form a plurality of gaps G in which an interstice d in a direction perpendicular to the projecting direction of the pillars 11 gradually decreases. The gap G has the interstice d on the order of 0 to several ten nm. The gap G is formed into a circular ring so as to surround its corresponding pillar 11 when seen in the projecting direction of the pillar 11, while the interstice d gradually decreases continuously at an end part G1 on the substrate 4 side. That is, the interstice d of the gap G in a direction perpendicular to the projecting direction of the pillar 11 gradually becomes smaller toward the substrate 4. Here, the base part 61 and protrusion 62 are connected to each other at the deepest part of the gap G, while a space S is formed at a root part of the pillar 11 (i.e., a corner part defined by the surface 8a of the support part 8 and the side face of the pillar 11). This space S is formed depending on a vapor deposition condition for forming the conductor layer 6 on the fine structure part 7 by vapor deposition and the like.

Figure 5:
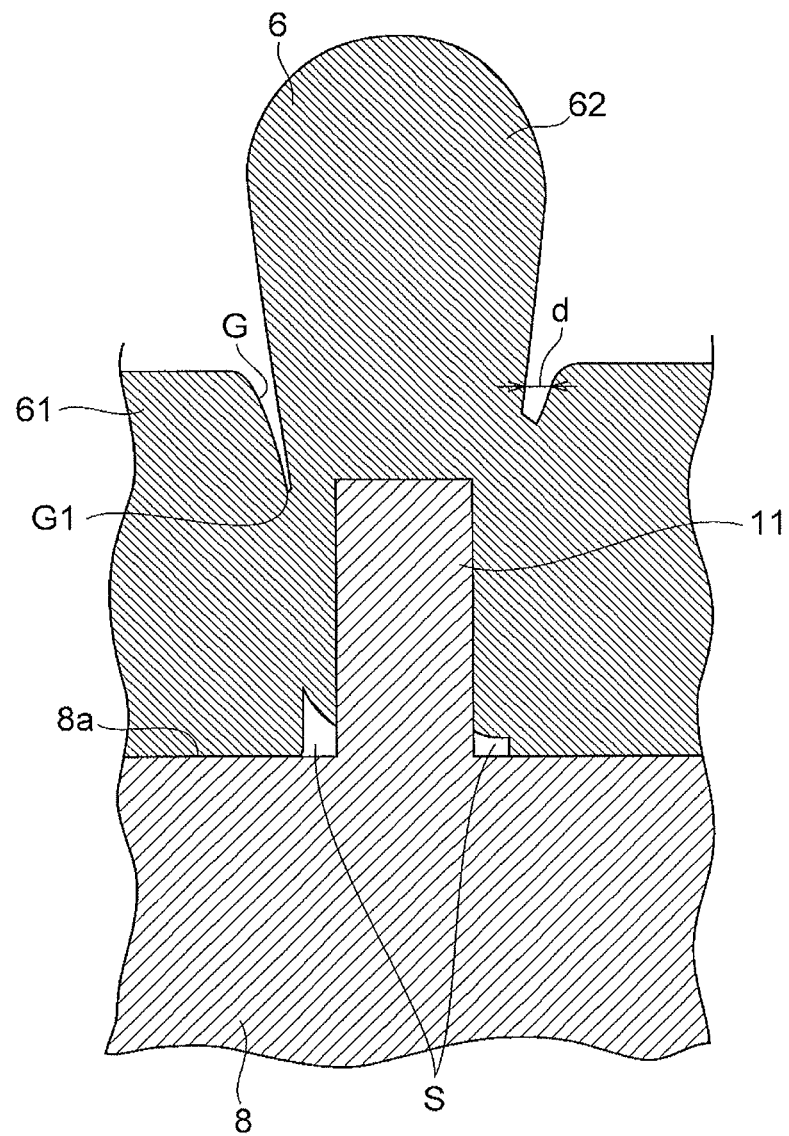
FIG. 5 is a vertical sectional view of the pillar and conductor layer in a modified example of the optical function part of FIG. 3.

As illustrated in FIG. 5, the thickness of the base part 61 may be greater than the height of the pillar 11, and the protrusion 62 may be formed on an extension of its corresponding pillar 11. In the conductor layer 6, the base part 61 and protrusion 62 form the gap G gradually decreasing the interstice d in a direction perpendicular to the projecting direction of the pillar 11 in this case as well.

The SERS unit 1 constructed as in the foregoing is used as follows. First, a ring-shaped spacer made of silicone, for example, is arranged on the front face 2a of the handling board 2 so as to surround the SERS element 3. Subsequently, a sample of a solution (or a dispersion of a powder sample in a solution such as water or ethanol) is dropped to the inside of the spacer with a pipette or the like, so as to arrange the sample on the optical function part 10. Then, for preventing the solvent from evaporating and for reducing the lens effect, a glass cover is mounted on the spacer and brought into close contact with the solution sample.

Next, the SERS unit 1 is set in a Raman spectroscopic analyzer, and the sample arranged on the optical function part 10 is irradiated with excitation light through the glass cover. This generates surface-enhanced Raman scattering at the interface between the optical function part 10 and sample, whereby surface-enhanced Raman scattering light derived from the sample is enhanced and released. Hence, the Raman spectroscopic analyzer enables Raman spectroscopy with high accuracy.

Not only the above-mentioned method, but the following methods may also be used for arranging the sample on the optical function part 10. For example, while holding the handling board 2, the SERS element 3 may be dipped in and lifted from the solution sample (or a dispersion of a powder sample in a solution such as water or ethanol), and then the sample may be blown to dry. A minute amount of the solution sample (or a dispersion of a powder sample in a solution such as water or ethanol) may be dropped onto the optical function part 10 and left to dry. A powder sample may be dispersed as it is on the optical function part 10.

An example of methods for manufacturing the SERS element 3 will now be explained. First, as illustrated in (a) of FIG. 6, a master mold MM and a film base F are prepared. The master mold MM includes a fine structure part M7 corresponding to the fine structure part 7 and a support part M8 for supporting the fine structure part M7. A plurality of fine structure parts M7 are arranged in a matrix on the support part M8. Subsequently, as illustrated in (b) of FIG. 6, the film base F is pressed against the master mold MM and pressurized and heated in this state, so as to transfer a pattern of the plurality of fine structure parts M7 to the film base F. Then, as illustrated in (c) of FIG. 6, the film base F is released from the master mold MM, so as to yield a replica mold (replica film) RM having the pattern of the plurality of fine structure parts M7 transferred thereto. The replica mold RM may also be one formed by applying a resin (examples of which include resins based on epoxy, acrylics, fluorine, silicone, and urethane and inorganic/organic hybrid resins) onto the film base F. When the resin to be applied onto the film base F is UV-curable, the replica mold R can be obtained by curing the resin applied on the film base F by irradiation with UV (UV nanoimprinting) instead of thermal nanoimprinting.

Next, as illustrated in (a) of FIG. 7, a silicone wafer 40 to become the substrate 4 is prepared, and a UV-curable resin is applied onto a front face 40a of the silicon wafer 40, so as to form a nanoimprinting layer 50 to become the molded layer 5 on the silicone wafer 40. Subsequently, as illustrated in (b) of FIG. 7, the replica mold RM is pressed against the nanoimprinting layer 50, and the nanoimprinting layer 50 is irradiated with UV in this state, so as to be cured, whereby the pattern of the replica mold RM is transferred to the nanoimprinting layer 50. Then, as illustrated in (c) of FIG. 7, the replica mold RM is released from the nanoimprinting layer 50, so as to yield the silicone wafer 40 formed with a plurality of fine structure parts 7.

Next, a film of a metal such as Au or Ag is produced on the molded layer 5 by vapor deposition, so as to form the conductor layer 6. Subsequently, the silicone wafer 40 is cut for each fine structure part 7 (i.e., for each optical function part 10), whereby a plurality of SERS elements 3 are obtained. For yielding the SERS unit 1, it is sufficient for the SERS element 3 manufactured as mentioned above to be attached onto the handling board 2.

The fine structure part 7 may be formed on the substrate 4 by etching using a mask having a two-dimensional pattern formed by photoetching, electron beam lithography, or the like instead of the above-mentioned nanoimprinting. In either case, forming the conductor layer 6 on the fine structure part 7 by vapor deposition can produce the conductor layer 6 with the nano-order gaps G with a favorable reproducibility in a simple process, thereby enabling mass production of the SERS element 3.

In the conductor layer 6 constituting the optical function part 10 in the SERS element 3, a plurality of gaps G in which the interstice d in a direction perpendicular to the projecting direction of the pillar 11 gradually decreases are formed by the base part 61 and protrusions 62 as explained in the foregoing. The gaps G formed in the conductor layer 6 favorably function as nanogaps (in particular in a part where the interstice d of the gaps G is 20 nm or less) where electric fields are locally enhanced. Therefore, the SERS element 3 can increase the intensity of surface-enhanced Raman scattering by favorable nanogaps.

Since a plurality of pillars 11 are arranged periodically along the front face 4a of the substrate 4, the intensity of surface-enhanced Raman scattering can be increased.

The gap G is formed so as to surround the pillar 11 when seen in the projecting direction of the pillar 11, while the interstice d gradually decreases at the end part on the substrate 4 side, whereby the gaps G favorably functioning as nanogaps can be increased.

Since the interstice of the gap G gradually decreases continuously, the gap G can securely function as a nanogap.

Since the protrusion 62 has a form constricted at the end part on the substrate 4 side, the gap G gradually decreasing the interstice d in a direction perpendicular to the projecting direction of the pillar 11 can be obtained easily and securely.

Figure 8:
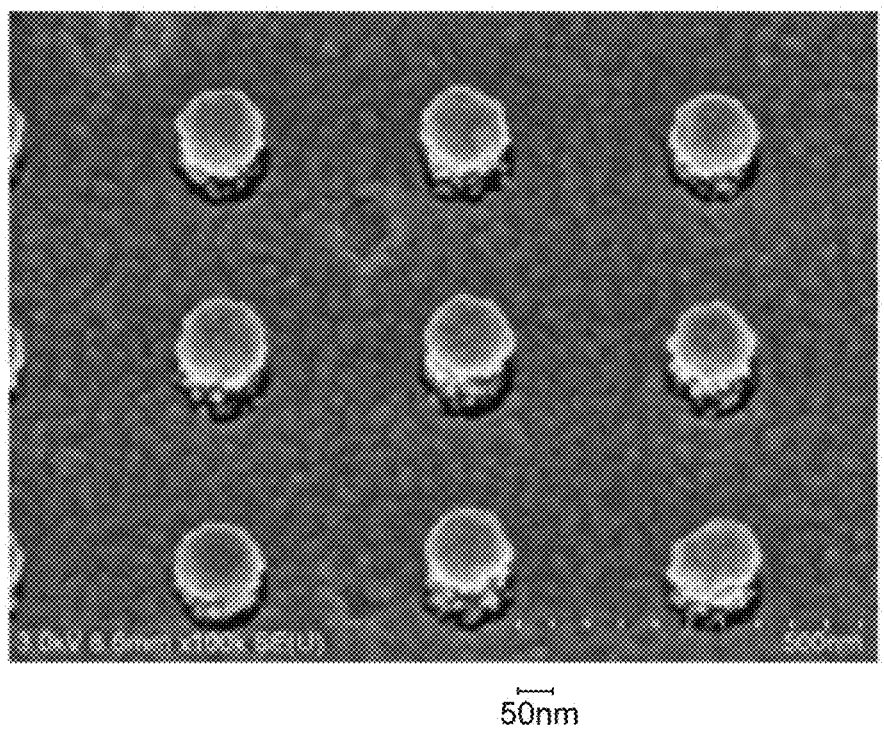
FIG. 8 is a SEM photograph of the optical function part in the surface-enhanced Raman scattering element of Example 1.
Figure 9:
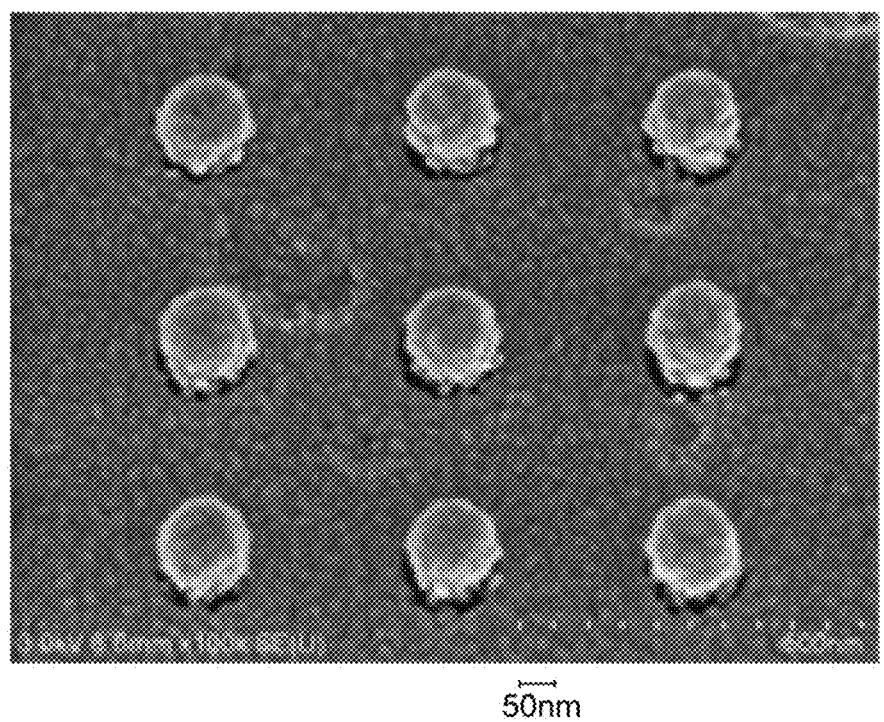
FIG. 9 is a SEM photograph of the optical function part in the surface-enhanced Raman scattering element of Example 2.
Figure 10:
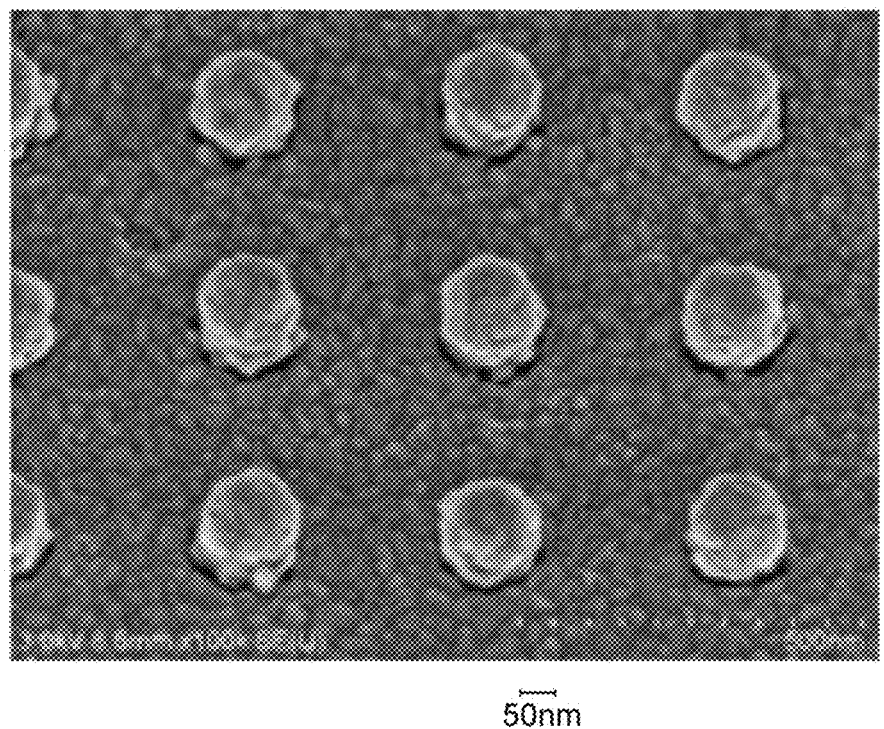
FIG. 10 is a SEM photograph of the optical function part in the surface-enhanced Raman scattering element of Example 3.
Figure 11:
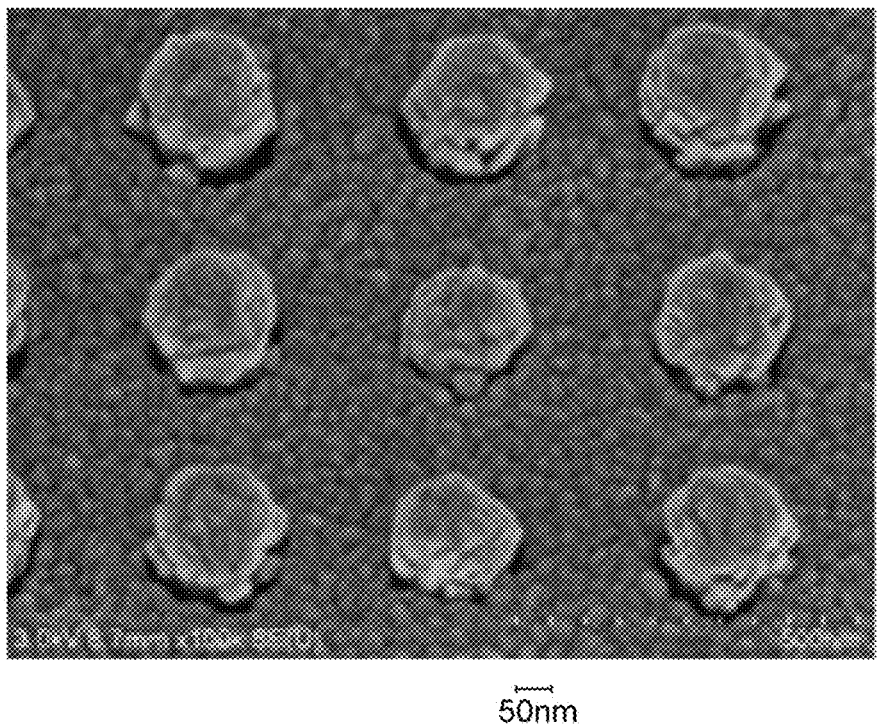
FIG. 11 is a SEM photograph of the optical function part in the surface-enhanced Raman scattering element of Example 4.

Examples of the SERS element 3 having the pillar 11 and conductor layer 6 illustrated in FIGS. 4 and 5 will now be explained. FIG. 8 is a SEM photograph of the optical function part in the SERS element of Example 1. In Example 1, Au was vapor-deposited as a conductor layer with a thickness of 30 nm. FIG. 9 is a SEM photograph of the optical function part in the SERS element of Example 2. In Example 2, Au was vapor-deposited as a conductor layer with a thickness of 50 nm. FIG. 10 is a SEM photograph of the optical function part in the SERS element of Example 3. In Example 3, Au was vapor-deposited as a conductor layer with a thickness of 100 nm. FIG. 11 is a SEM photograph of the optical function part in the SERS element of Example 4. In Example 4, Au was vapor-deposited as a conductor layer with a thickness of 200 nm. Each of FIGS. 8 and 9 is a SEM photographs capturing the optical function part in a direction tilted by 30° from a direction perpendicular to the surface of the substrate.

The SERS elements of Examples 1 to 4 were made as follows. First, using a mold in which holes, each having a hole diameter of 120 nm and a hole depth of 180 nm, were arranged in a square lattice at a hole interval (distance between center lines of holes adjacent to each other) of 360 nm, a resin on a substrate made of glass was molded by nanoimprinting, so as to produce a fine structure part. In thus produced fine structure part, the pillars had a diameter of 120 nm, a height of 150 nm, and a pillar pitch (distance between center lines of pillars adjacent to each other) of 360 nm.

Next, a film of Ti was formed as a buffer layer by resistance heating vacuum vapor deposition on the produced fine structure part. The film forming condition for the buffer layer was "film thickness: 2 nm; vapor deposition rate: 0.02 nm/s; degree of vacuum during film forming: $2 \times 10^{-5}$ torr; substrate rotation: none; substrate temperature control: none." Subsequently, a film of Au was formed as a conductor layer by resistance heating vacuum vapor deposition on the buffer layer, so as to yield the SERS elements of Examples 1 to 4. The film forming condition for the conductor layer was "film thickness: as mentioned above; vapor deposition rate: 0.02 nm/s; degree of vacuum during film forming: $1.5 \times 10^{-5}$ torr; substrate rotation: none; substrate temperature control: none."

The gap formed by the base part and protrusion (gap gradually decreasing the interstice in a direction perpendicular to the projecting direction of the protrusion) is easier to form under the following conditions. First, resistance heating vacuum vapor deposition or electron beam vapor deposition is preferred to sputtering. It seems that resistance heating vacuum vapor deposition or electron beam vapor deposition employs a vapor deposition source having a relatively small heating part, so that vapor deposition materials fly to the substrate with such favorable directivity as to be less likely to reach side faces of pillars, whereby vapor-deposited materials piled on leading end parts of the pillars are likely to cast shadows on bottom parts of the pillars. In sputtering, on the other hand, vapor deposition materials seem to fly from a relatively large gold target surface toward the side faces of pillars as well, thereby making it harder for gaps to occur in the bottom parts of the pillars. Second, it is preferable for the substrate to stand still during vapor deposition. For mass production (for processing a plurality of wafers in a vapor deposition system), however, better stability in film thickness is attained when revolving the wafers about the vapor deposition source while keeping a fixed angle thereto without rotating them.

As illustrated in FIG. 8, ring-slit-shaped gaps are generated in root parts of the protrusions of the conductor layer in Example 1 (with the Au film thickness of 30 nm). As illustrated in FIGS. 9 to 11, as the Au film thickness increases successively in Example 2 (the Au film thickness of 50 nm), Example 3 (the Au film thickness of 100 nm), and Example 4 (the Au film thickness of 200 nm), the protrusions in the conductor layer become laterally thicker, and the ring-slit-shaped gaps formed in the root parts of the protrusions are also made greater. Thus, the ring-slit-shaped gaps are generated either when the thickness of the conductor layer (i.e., the thickness of the base part of the conductor layer) is smaller (Examples 1 to 3) or greater (Example 4) than the height of the pillars.

Figure 12:
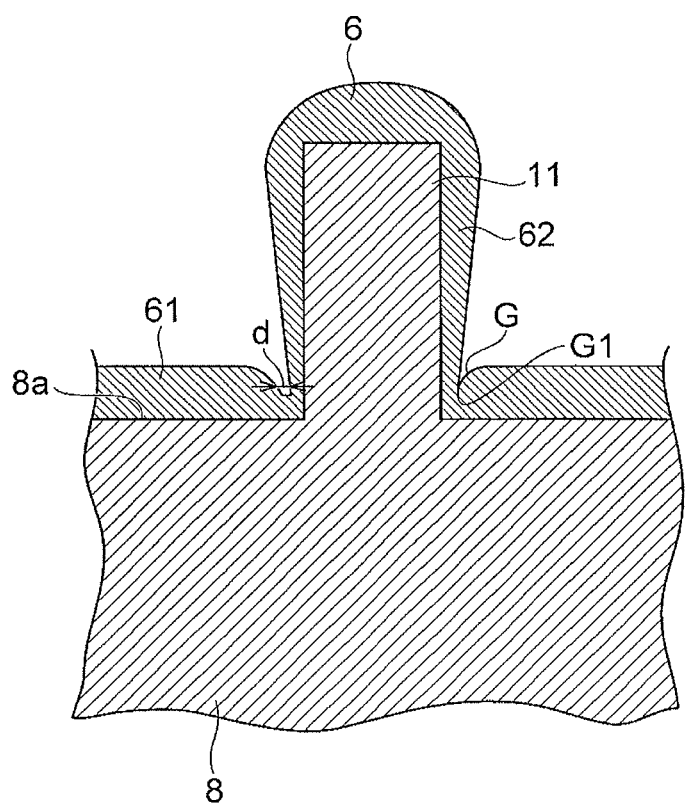
FIG. 12 is a vertical sectional view of the pillar and conductor layer in a modified example of the optical function part of FIG. 3.
Figure 13:
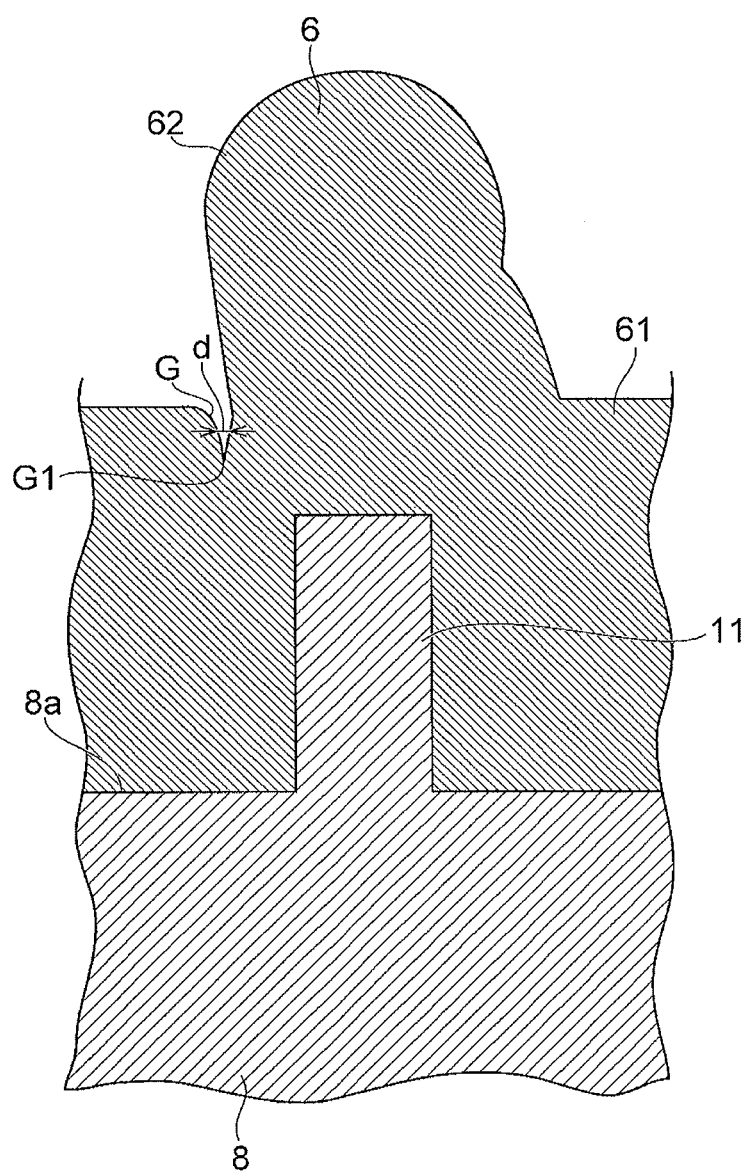
FIG. 13 is a vertical sectional view of the pillar and conductor layer in a modified example of the optical function part of FIG. 3.

Modified examples of the optical function part 10 of FIG. 3 will now be explained. As illustrated in FIG. 12, when the thickness of the base part 61 is smaller than the height of the pillar 11, the root part of the pillar 11 (i.e., the corner part defined by the surface 8a of the support part 8 and the side face of the pillar 11) may be free of the space S illustrated in FIG. 4. Similarly, as illustrated in FIG. 13, the root part of the pillar 11 may be free of the space S illustrated in FIG. 5 when the thickness of the base part 61 is greater than the height of the pillar 11.

Examples of the SERS element 3 having the pillar 11 and conductor layer 6 illustrated in FIGS. 12 and 13 will now be explained. FIG. 14 is a SEM photograph of the optical function part in the SERS element of Example 5. FIG. 14 is a SEM photograph of the optical function part in the SERS element of Example 5. FIG. 14 is a SEM photograph capturing the optical function part in a direction tilted by 30° from a direction perpendicular to the surface of the substrate.

The SERS element of Example 5 was made as follows. First, as with the above-mentioned Examples 1 to 4, a resin on the substrate made of glass was molded by nanoimprinting, so as to make a fine structure part. In thus produced fine structure part, the pillars had a diameter of 120 nm, a height of 150 nm, and a pillar pitch (distance between center lines of pillars adjacent to each other) of 360 nm.

Next, a film of Ti was formed as a buffer layer by resistance heating vacuum vapor deposition on the produced fine structure part. The film forming condition for the buffer layer was "film thickness: 2 nm; vapor deposition rate: 0.02 nm/s; degree of vacuum during film forming: $2 \times 10^{-5}$ torr; substrate rotation: none; substrate temperature control: none." Subsequently, a film of Au was formed as a conductor layer by sputtering on the buffer layer, so as to yield a continuous Au film as illustrated in (a) of FIG. 14. The film forming condition for the conductor layer was "film thickness: 50 nm; film forming time: 5 min; atmosphere gas: air; substrate rotation: none; substrate temperature control: none." Then, a film of Au was formed as a conductor layer by resistance heating vapor deposition method on the continuous Au film, so as to yield the SERS element of Example 5 as illustrated in (b) of FIG. 14. The film forming condition for the continuous Au film was "film thickness: 50 nm; vapor deposition rate: 0.02 nm/s, degree of vacuum during film forming: $1.5 \times 10^{-5}$ torr; substrate rotation: none; substrate temperature control: none."

As illustrated in (a) of FIG. 14, the continuous Au film formed by sputtering is a film which is continuous so as to cover the whole surface of the fine structure part. As illustrated in (b) of FIG. 14, ring-slit-shaped gaps are generated in root parts of the protrusions of the conductor layer also when a film of Au is formed by resistance heating vacuum vapor deposition as a conductor layer on the continuous Au film.

Figure 15:
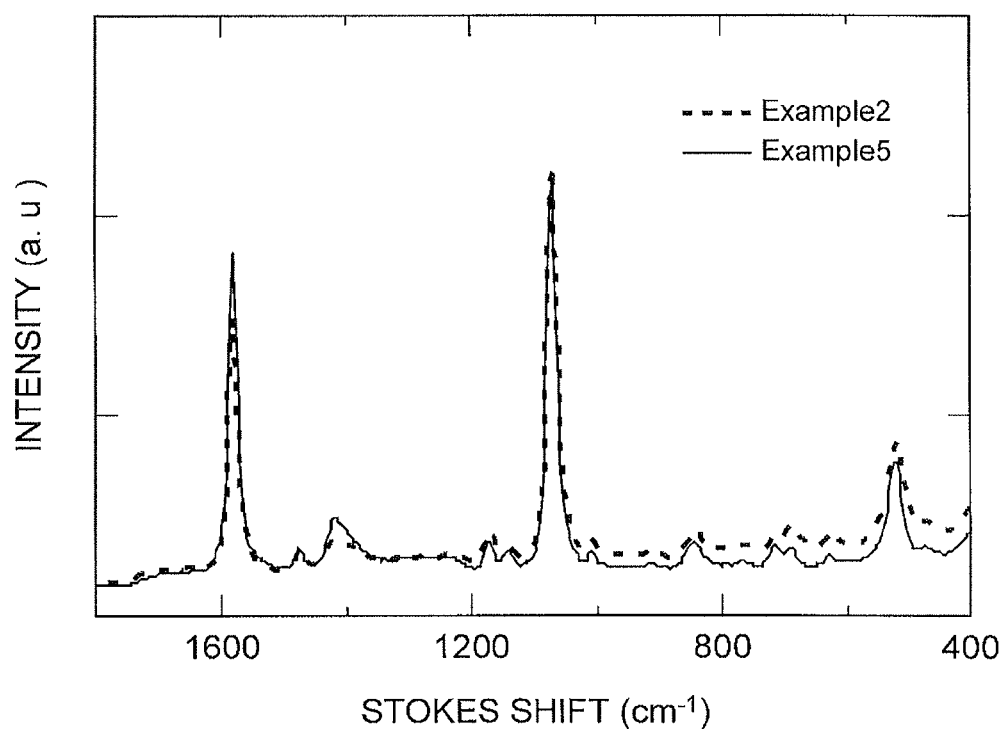
FIG. 15 is a graph illustrating relationships between Stokes shift and signal intensity concerning the surface-enhanced Raman scattering elements of Examples 2 and 5.

FIG. 15 is a graph illustrating relationships between Stokes shift and signal intensity concerning the surface-enhanced Raman scattering elements of Examples 2 and 5. Here, the SERS elements of Examples 2 and 5 were dipped in an ethanol solution of mercaptobenzonic acid (1 mM) for two hours, then rinsed with ethanol, and dried with a nitrogen gas, so that a sample was arranged on the optical function part of the SERS element. The sample was subjected to Raman spectrometry with excitation light having a wavelength of 785 nm. This resulted in SERS spectra of mercaptobenzonic acid with substantially the same signal intensity in both Examples 2 and 5 as illustrated in FIG. 15. The intensity of surface-enhanced Raman scattering is seen to increase regardless of whether or not there is the space S in root parts of the pillar 11 (i.e., the corner part defined by the surface 8a of the support part 8 and the side face of the pillar 11).

Figure 16:
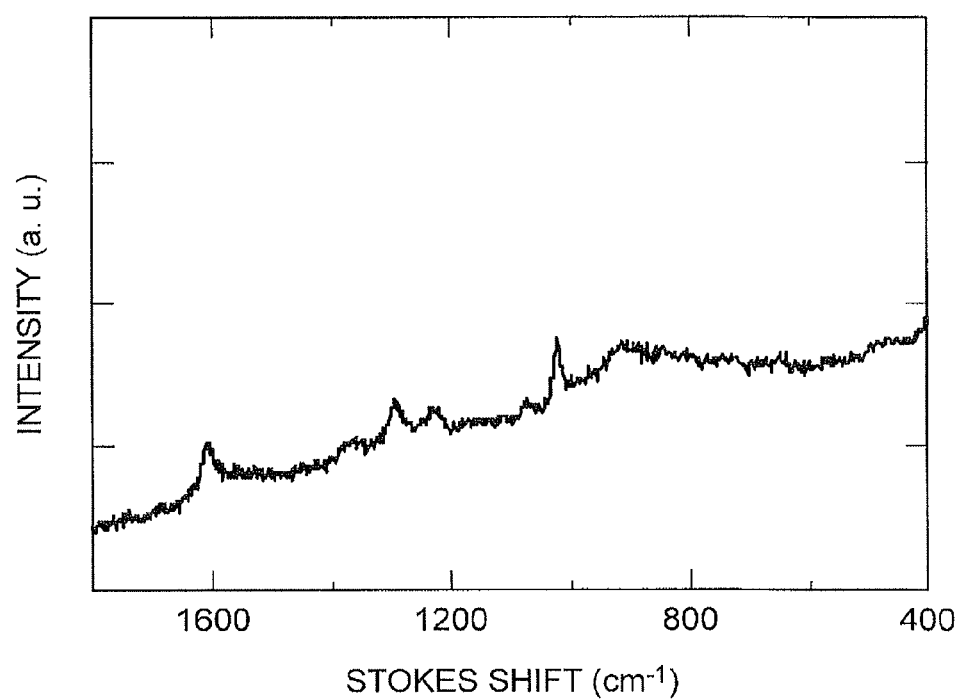
FIG. 16 is a graph illustrating a relationship between Stokes shift and signal intensity concerning the surface-enhanced Raman scattering element of Example 2.

FIG. 16 is a graph illustrating a relationship between Stokes shift and signal intensity concerning the surface-enhanced Raman scattering element of Example 2. Here, an aqueous solution of 4,4'-bipyridyl (0.1 μM) was dropped onto the optical function part of the SERS element of Example 2, and a glass cover was put thereon as a lid so as to keep it from drying, whereby a sample was arranged on the optical function part. The sample was subjected to Raman spectrometry with excitation light having a wavelength of 785 nm. This resulted in a SERS spectrum of 4,4'-bipyridyl as illustrated in FIG. 16.

In FIG. 17, (a) and (b) are graphs illustrating relationships between pillar pitch and signal intensity in the surface-enhanced Raman scattering elements of Examples 2 and 5, respectively. These graphs show results concerning a peak intensity at a Stokes shift of 1072 cm$^{-1}$ in the case of FIG. 15. It is seen from (a) and (b) of FIG. 17 that the intensity of surface-enhanced Raman scattering depends on the pillar pitch (distance between the center lines of pillars adjacent to each other) and that the pillar pitch is preferably 250 nm to 800 nm in order to increase the intensity of surface-enhanced Raman scattering. These plots are substantially applicable even when the diameter of pillars varies. By "duty" in the graphs of (a) and (b) in FIG. 17 is meant the ratio between the pillar width and the space between pillars in the fine structure part.

While an embodiment of the present invention is explained in the foregoing, the present invention is not limited to the above-mentioned embodiment. For example, the pillars 11 may be arranged one-dimensionally instead of two-dimensionally or in a triangular lattice instead of a square lattice. The cross-sectional form of the pillars 11 is not limited to circles, but may be ellipses or polygons such as triangles and quadrangles. Thus, without being restricted to those mentioned above, various materials and forms can be employed for constituents of the SERS element 3 and SERS unit 1.

When attention is focused on a pair of projections (those corresponding to the pillars 11) adjacent to each other, the width of the gap formed by the based part and the protrusion is smaller than the distance between the conductor layer formed on the outer surface of one projection and that formed on the outer surface of the other projection. This can easily and stably form such a narrow gap (gap favorably functioning as a nanogap) as to be unattainable by the configuration of the fine structure part alone.

The fine structure part 7 may be formed on the front face 4a of the substrate 4 either indirectly with the support part 8, for example, interposed therebetween as in the above-mentioned embodiment or directly. The conductor layer 6 may be formed on the fine structure part 7 either indirectly with a layer such as a buffer metal (Ti, Cr, or the like) for improving the adhesion of a metal to the fine structure part 7, for example, interposed therebetween or directly.

Figure 18:
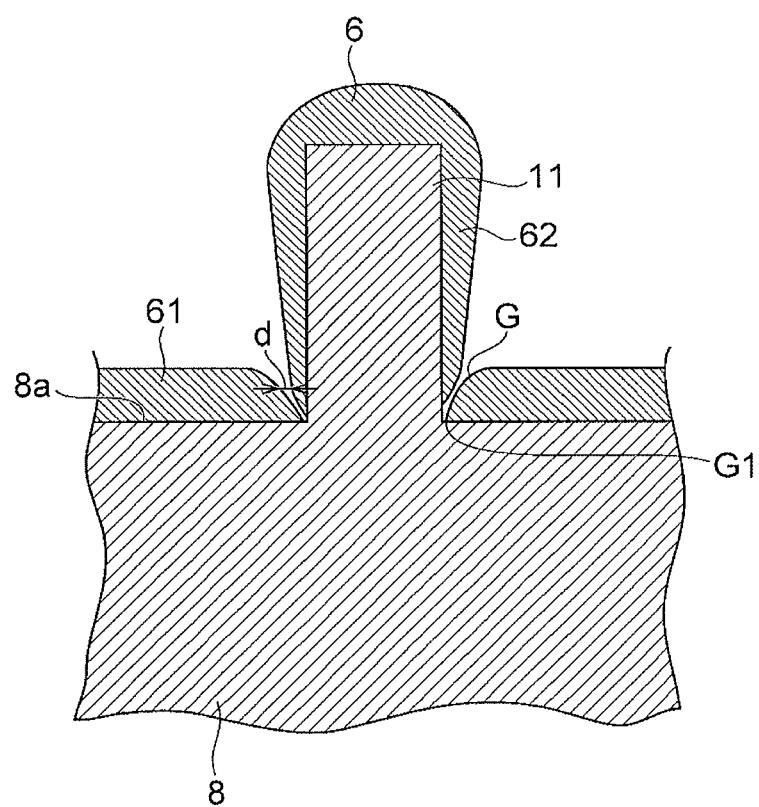
FIG. 18 is a vertical sectional view of the pillar and conductor layer in a modified example of the optical function part of FIG. 3.

As illustrated in FIG. 18, the base part 61 and protrusion 62 may be separated from each other at the deepest part of the gap G. An end part on the substrate 4 side of the protrusion 62 located closer to the substrate than is the upper face of the base part 61 also forms a favorable nanogap with the base part 61 while curving radially of the pillar 11, which can increase the intensity of surface-enhanced Raman scattering in this case as well.

INDUSTRIAL APPLICABILITY

The present invention can provide a surface-enhanced Raman scattering element which can increase the intensity of surface-enhanced. Raman scattering by a favorable nanogap.

REFERENCE SIGNS LIST

3: SERS element (surface-enhanced Raman scattering element); 4: substrate; 4a: front face (principal surface); 6: conductor layer; 7: fine structure part; 10: optical function part; 11: pillar (projection); 61: base part; 62: protrusion; G: gap.

The invention claimed is:

1. A surface-enhanced Raman scattering element comprising:
    a substrate having a principal surface;
    a fine structure part formed on the principal surface and having a plurality of projections; and
    a conductor layer formed on the fine structure part and constituting an optical function part for generating surface-enhanced Raman scattering;
    wherein the conductor layer has a base part formed along the principal surface and a plurality of protrusions protruding from the base part at respective positions corresponding to the projections; and
    wherein the base part and the protrusions form a plurality of gaps in the conductor layer, each of the gaps having an interstice gradually decreasing in a direction perpendicular to the projecting direction of a projection of said plurality of projections,
    wherein each of the gaps has a depth in the projecting direction of the projection equal to or smaller than a thickness of the base part, and
    wherein an end part of a protrusion on the substrate side of the protrusion is located closer to the substrate than is an upper face of the base part, the end part being an outer circumferential portion at the substrate side of the protrusion, the end part being formed along a circumferential direction of the projection.

2. A surface-enhanced Raman scattering element according to claim 1, wherein the projections are arranged periodically along the principal surface.

3. A surface-enhanced Raman scattering element according to claim 1, wherein the gaps are formed so as to surround the respective projections when seen in the projecting direction of the projections and each of the gaps have the interstice gradually decreasing at an end part on the substrate side.

4. A surface-enhanced Raman scattering element according to claim 1, wherein the interstice of the gap gradually decreases continuously.

5. A surface-enhanced Raman scattering element according to claim 1, wherein the protrusion has a form constricted at an end part on the substrate side.

6. A surface-enhanced Raman scattering element according to claim 1, wherein the base part has a thickness smaller than a height of the projections.

7. A surface-enhanced Raman scattering element according to claim 1, wherein the base part has a thickness greater than a height of the projections.

8. A surface-enhanced Raman scattering element according to claim 1, wherein the base part and the protrusion are connected to each other at the deepest part of the gap.

9. A surface-enhanced Raman scattering element according to claim 1, wherein the base part and the protrusion are separated from each other at the deepest part of the gap.

* * * * *